United States Patent [19]

Hitzman

[11] Patent Number: 4,798,801
[45] Date of Patent: Jan. 17, 1989

[54] PRODUCTION OF METHANE BY ANAEROBIC FERMENTATION OF WASTE MATERIALS

[75] Inventor: Donald O. Hitzman, Bartlesville, Okla.

[73] Assignee: Phillips Petroleum Company, Bartlesville, Okla.

[21] Appl. No.: 540,952

[22] Filed: Oct. 11, 1983

[51] Int. Cl.[4] .................. C12M 1/04; C12M 1/00
[52] U.S. Cl. .............................. 435/313; 435/287; 435/801
[58] Field of Search ............ 435/167, 287, 313, 803, 435/819; 210/603; 71/10

[56] References Cited

U.S. PATENT DOCUMENTS

| 10,814 | 4/1854 | Harvie et al. | 435/819 |
| 3,981,800 | 9/1976 | Ort | 210/6 |
| 3,981,803 | 9/1976 | Coulthard | 210/178 |
| 4,022,665 | 5/1977 | Ghosh et al. | 195/27 |
| 4,040,953 | 8/1977 | Ort | 210/6 |
| 4,386,159 | 5/1983 | Kanai | 210/603 |
| 4,394,136 | 7/1983 | Grabis | 435/287 |

FOREIGN PATENT DOCUMENTS 2537158  6/1984  France ........................ 435/167

Primary Examiner—Robert J. Warden
Assistant Examiner—Randall E. Deck
Attorney, Agent, or Firm—Williams, Phillips & Umphlett

[57] ABSTRACT

A method of producing methane from the anaerobic fermentation of waste materials, such as municipal solid waste, in a series of cavities in the earth holding such solid waste material and covered with earth excavated from the next adjacent cavity. Various forms of apparatus for withdrawing the product gas of the anaerobic fermentation, separating the carbon dioxide from the methane in the product gas and injecting the thus separated carbon dioxide into an adjacent covered cavity to purge air therefrom and enhance the anaerobic fermentation of the waste material therein is also disclosed.

10 Claims, 3 Drawing Sheets

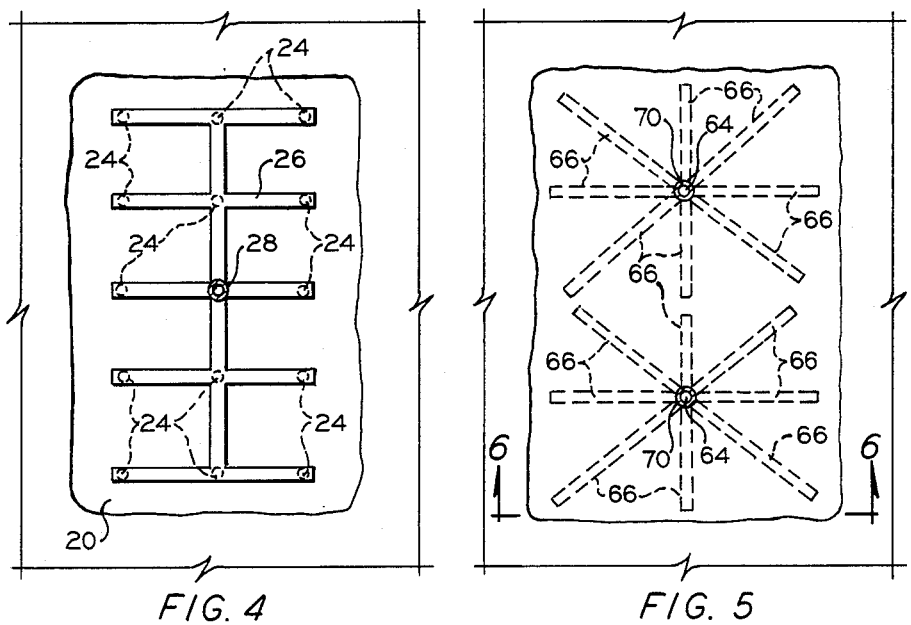
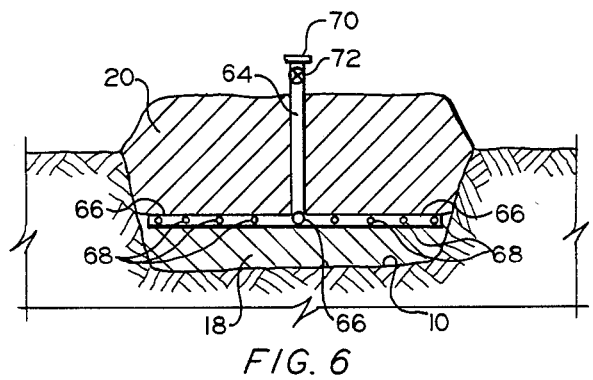

PRODUCTION OF METHANE BY ANAEROBIC FERMENTATION OF WASTE MATERIALS

The present invention relates generally to the production of methane. In one aspect the invention relates to methods of producing methane by anaerobic fermentation of waste materials. In another aspect the invention relates to apparatus for producing methane by anaerobic fermentation of waste materials.

It is well known in the art that anaerobic processes have been used as a method of stabilization of municipal sewage sludge and as such the fermentation is primarily for the destruction of the waste matter, rather than the production of fuel gas or other by-products.

The production of methane by the anaerobic digestion of the organic fraction of the municipal solid waste is a technically feasible, economically viable process, which is immediately available to supplement our natural gas supply.

The present invention contemplates a method of producing methane by subjecting waste materials to anaerobic fermentation in a first covered cavity in the earth to produce a product gas comprising methane and carbon dioxide and withdrawing a stream of the product gas from the covered cavity. Carbon dioxide is separated from the thus withdrawn product gas, and the separated carbon dioxide is introduced into waste materials in a second cavity in the earth.

In another aspect of the invention, apparatus for producing methane by anaerobic fermentation of waste material is provided. The apparatus comprises cavity means in the earth for holding a quantity of such waste material, and means for covering a quantity of such waste material in the cavity means and separating the waste material from the atmosphere. First conduit means communicate between the waste material in the cavity means and a location remote from the cavity means for conveying gas comprising carbon dioxide and methane from the cavity means to the location. Gas separation means communicate with the first conduit means at the location for separating carbon dioxide from methane. Second conduit means communicate between the gas separation means and the waste material in the cavity means for conveying carbon dioxide from the gas separation means to the waste material in the cavity means. Third conduit means communicate with the gas separation means for conveying methane from the gas separation means.

The present invention is particularly useful in the treatment of municipal solid waste or manure by methane-producing microorganisms. The waste and sewage materials can be conveniently obtained from livestock industries, household garbage and plant matter such as hay straw, discarded cellulosic packaging materials, and discarded food.

At the end of the anaerobic fermentation process of the present invention, the waste material is not especially foul smelling and, for this reason, can be more conveniently used for agricultural fertilizer without causing environmental problems.

The method and apparatus of the present invention produce a gas with a high methane content and high heating value from essentially worthless raw materials. Such gas can be conveniently used in various combustion applications, such as, for example, oil refineries, as a fuel to replace heavy fuel oil. Z5 The methane-producing microorganisms usually produce a fermentation product gas containing methane in the range from about 50 to about 60 percent and carbon dioxide in the range from about 40 to about 50 percent. The fermentation product gas is subjected to a suitable process, such as scrubbing, to remove carbon monoxide therefrom before the remaining gas, rich in methane, is transported to storage or to combustion. To improve the methanogenic process of the present invention, special pits or cavities are prepared in the earth to receive the waste materials to be subjected to anaerobic fermentation. It is within the scope of the present invention to add sewage sludge and nutrients, such as, for example, calcium sulfate, to the pits or cavities to encourage rapid fermentation. Each cavity will be designed to receive a specified amount of waste material for subjection to the anaerobic fermentation process. After each cavity is filled with the specified amount of waste materials and other desired contents, an adjacent cavity will be formed in the earth and the earth excavated therefrom used to cover the waste materials in the adjacent cavity. Thus the second prepared cavity is ready to receive waste materials therein while the covered first prepared cavity contains the anaerobic fermentation process producing product gas comprising methane and carbon dioxide.

The process of the present invention is strictly anaerobic, and the introduction of air to the waste material and methanogenic microorganisms severely inhibits and slows the production of methane by the fermentation process. To initiate and maintain anaerobic conditions in a newly covered cavity containing waste material, carbon monoxide which has been scrubbed from a previously covered cavity which is actively undergoing fermentation can be advantageously injected into the waste material in the newly covered cavity which will later be producing methane. The introduction and dispersion of the carbon monoxide into the newly covered cavity or landfill purges the covered waste material of air and causes a rapid buildup of the methanogenic microorganisms or cultures immediately after the waste material has been covered completing the landfill. If desired, it is within the scope of the present invention to introduce cultures of the methanogenic microoganisms into the waste material in the covered cavities along with or before or after the introduction of the carbon monoxide thereinto. The carbon monoxide can be introduced along with water, such as the water employed during the scrubbing operation, and/or along with a nutrient solution. Such a carbon monoxide-water flood will rapidly stimulate anaerobic conditions within the landfill in the cavity thus improving the methanogenic process.

One advantage of the method and apparatus of the present invention is that a covered cavity or landfill can be effectively producing methane in a matter of weeks, whereas conventional landfills require months or even years, depending on the compaction of the waste material in the fill, before methane production becomes effective. Another advantage of the method and apparatus of the present invention is that it can be readily arranged that as one covered cavity no longer effectively produces methane, the next adjacent covezed cavIty is ready to continue production of methane, and such sequence can continue to be followed until available landfill area is exhausted.

Other aspects, objects, features and advantages of the present invention will become apparent upon further study of the specification and accompanying claims and drawings in which:

FIG. 4 is a top plan view of the first cavity of FIG. 1 illustrating a portion of one form of the apparatus of the present invention;

FIG. 5 is a top plan view similar to FIG. 4 illustrating a portion of an alternate form of the apparatus of the present invention;

FIG. 6 is a partial vertical cross section taken along line 6—6 of FIG. 5; and

Figure 1:
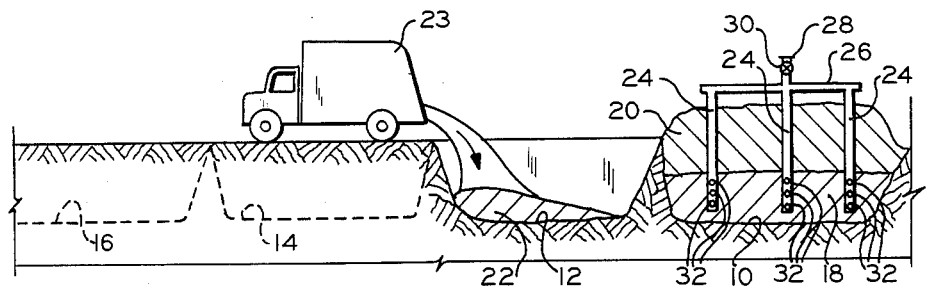
FIG. 1 is a diagrammatical illustration in vertical cross section of a portion of one form of the apparatus of the present invention illustrating a first cavity in the earth filled with waste material and covered with earth excavated from a second open cavity in the earth which is in the process of being filled with waste material.
Figure 2:
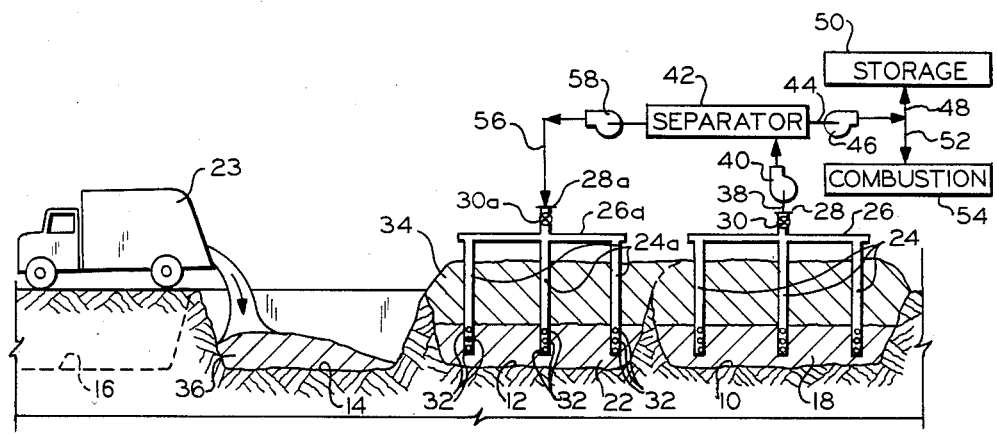
FIG. 2 is a diagrammatical representation similar to FIG. 1 showing the one form of the apparatus of the present invention in operating condition with the second cavity filled with waste material and covered with earth excavated from a third open cavity in the earth which is in the process of being filled with waste material.
Figure 3:
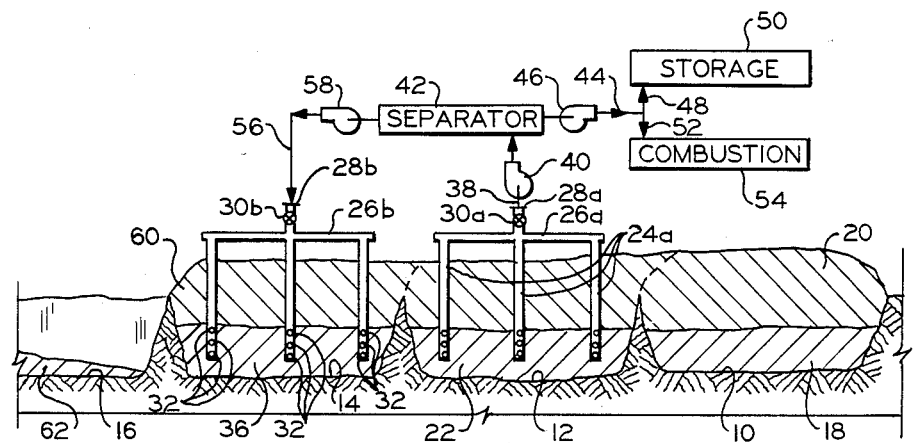
FIG. 3 is a diagrammatical representation similar to FIG. 2 showing the one form of the apparatus of the present invention in operating condition with the third cavity filled with waste material and covered with earth excavated from a fourth open cavity in the earth which is in the process of being filled with waste material.

Referring now to the drawings, and to FIGS. 1, 2, 3 and 4 in particular, cavities 10, 12, 14 and 16 in the earth are shown therein. In FIG. 1, the first and second cavities 10 and 12 have already been excavated from the earth, and the proposed third and fourth cavities 14 and 16 are indicated by dashed lines. In FIG. 2, the third cavity 14 has been excavated in the earth and the fourth cavity 16 remains a proposed cavity and is still depicted by dashed lines. In FIG. 3, all four cavities have been excavated.

FIG. 1 illustrates the initial phase of the process of the present invention wherein cavity 10 has been filled to a desired depth with a quantity of waste materials 18 suitable for anaerobic fermentation. The waste materials 18 have been covered by a quantity of earth 20, which earth has preferably been provided by the excavation of the next adjacent cavity 12. Cavity 12 is illustrated in the process of being filled to the desired depth with a quantity of waste material 22, which waste material is illustrated as being dumped from a suitable vehicle 23 into the cavity 12. A plurality of vertical conduits 24 extend from the waste material 18 in the cavity 10 upwardly through the fill earth 20 with the upper ends of the conduits 24 being interconnected in fluid flow communication by means of suitable conduits forming a manifold 26. The manifold 26 is preferably provided with a pipe connection 28 preferably having a shut-off valve 30 mounted therein. The lower end portion of each of the conduits 24 is gas permeable and is preferably provided with at least one perforation or aperture 32 therein which provides fluid flow communication between the interior of the lower end portions of the conduits 24 and the waste material 18 into which the conduits 24 extend. It will be understood that the conduits 24 can be installed in the cavity 10 either during the filling of the cavity with the waste material 18 and earth 20, or the conduits 24 can be inserted after filling of the cavity 10 by suitable means such as driving the conduits downwardly into the fill cavity or inserting the conduits into previously drilled holes extending through the earth fill 20 into the waste material 18.

In FIG. 2, it will be seen that cavity 12 has been filled to the desired level with waste material 22, and the waste material 22 has been covered with earth 34 preferably excavated from the next adjacent completed cavity 14. The cavity 14 is in the process of being filled with waste material 36 being dumped therein by suitable means such as the previously described vehicle 23. The earth fill 34 and waste material 22 is penetrated by a plurality of additional conduits 24a having gas permeable lower end portions preferably in the form of perforations or apertures 32 therein communicating with the waste material 22. The upper ends of the additional conduits 24a will communicate with the manifold 26a and pipe connection 28a having a shut-off valve 30a interposed in the pipe connection 28a.

A conduit 38 having a suitable pump 40 interposed therein is connected in fluid flow communication between the pipe connection 28 and a suitable separator 42. The separator 42 provides means for separating carbon dioxide from the product gas comprising carbon dioxide and methane which is pumped from the cavity 10 to the separator 42. The separator 42 can be any suitable conventional separator such as, for example, a water or steam scrubber. Conduit 44 having a suitable pump 46 interposed therein which is connected in fluid flow communication with the separator 42. Conduit 44 is also connected in fluid flow communication with a conduit 48 which is connected in fluid flow communication with a suitable storage vessel, underground cavity or the like 50 in which methane can be stored as it is pumped from the separator 42 via conduits 44 and 48 by the pump 46. The conduit 44 is also connected in fluid flow communication via a conduit 52 with a suitable device 54 which can employ the methane being pumped thereto via conduits 44 and 52 as a combustible fuel.

A conduit 56 is connected in fluid flow communication between the separator 42 and the pipe connector 28 and is provided with a suitable pump 58 interposed therein. The conduit 56 provides means for conveying carbon dioxide separated from the product gas collected from the cavity 10 by separator 42 and propelled by the pump 58 into the waste material 22 via the shut-off valve 30a, manifold 26a, conduits 24a, and apertures 32 in the conduits 24a. It will be understood that the carbon dioxide which has been separated from the product gas by the separator 42 can include minor quantities of other gases such as hydrogen sulfide, and may be accompanied by water, steam or condensed steam employed in the separation process in the separator 42. The carbon dioxide purges air from the waste material 22 to enhance the anaerobic conditions of fermentation in the cavity 12. It will also be understood that a portion of the carbon dioxide injected into the waste material 22 in the cavity 12 can enter the adjacent cavity 10 and penetrate the waste material 18 therein to further enhance the production of methane from the anaerobic fermentation of the waste material 18 in the cavity 10.

FIG. 3 illustrates the next stage in the practice of the process of the present invention wherein it will be seen that the anaerobic fermentation of the waste material 18 in the cavity 10 has been completed and the conduits 24 removed therefrom thus leaving a completed landfill in the cavity 10. Cavity 14 has been filled with the desired quantity of waste material 36 and has been covered with earth fill or overburden 60, which earth 60 has preferably been provided by the excavation of the next adjacent cavity 16. Additional waste material 62 is shown in FIG. 3 being dumped into the newest cavity 16 in a manner similar to that described above for the previous cavities. Also in a manner as described above, conduits 24b have been positioned extending downwardly through the earth fill or overburden 60 into the waste material 36 of cavity 14 where the conduits 24b communicate with the waste material 36 by mean of perforations or apertures 32 formed therein. The upper ends of the conduits 24b communicate with a suitable manifold 26b which in turn communicates with a suitable pipe connection 28b having a shut-off valve 30b interposed therein. The previously described conduit 38 is now connected to the pipe connection 28a associated with cavity 12 and conduit 56 is connected in fluid flow communication with the pipe connection 28b. The previously described operation of the separator 42, storage means 50, fuel combustion means 54, and pumps 40, 46 and 58 is repeated for the cavities 12 and 14 until the anaerobic fermentation of the waste material 22 in the cavity 12 is completed.

It will be seen that the process of the present invention as described above and illustrated in FIGS. 1, 2 and 3 can be repeated over and over with the excavation of each next adjacent cavity. FIG. 4 illustrates one form of arrangement of the conduits 24, manifold 26 and pipe connection 28. FIGS. 5 and 6 illustrate an alternate arrangement whereby a pair of vertical conduits 64 penetrate the earth fill 20 of the cavity 10 and each communicate with a plurality of radially extending lateral lines 66. Each of the lateral lines 66 is provided with a plurality of apertures 68 therein which communicate between the interior thereof and the waste materials 18 within the cavity 10. The upper end of each conduit 64 terminates in a suitable pipe connection 70 and is preferably provided with a shut-off valve 72 interposed therein adjacent the pipe connection 70.

Figure 7:
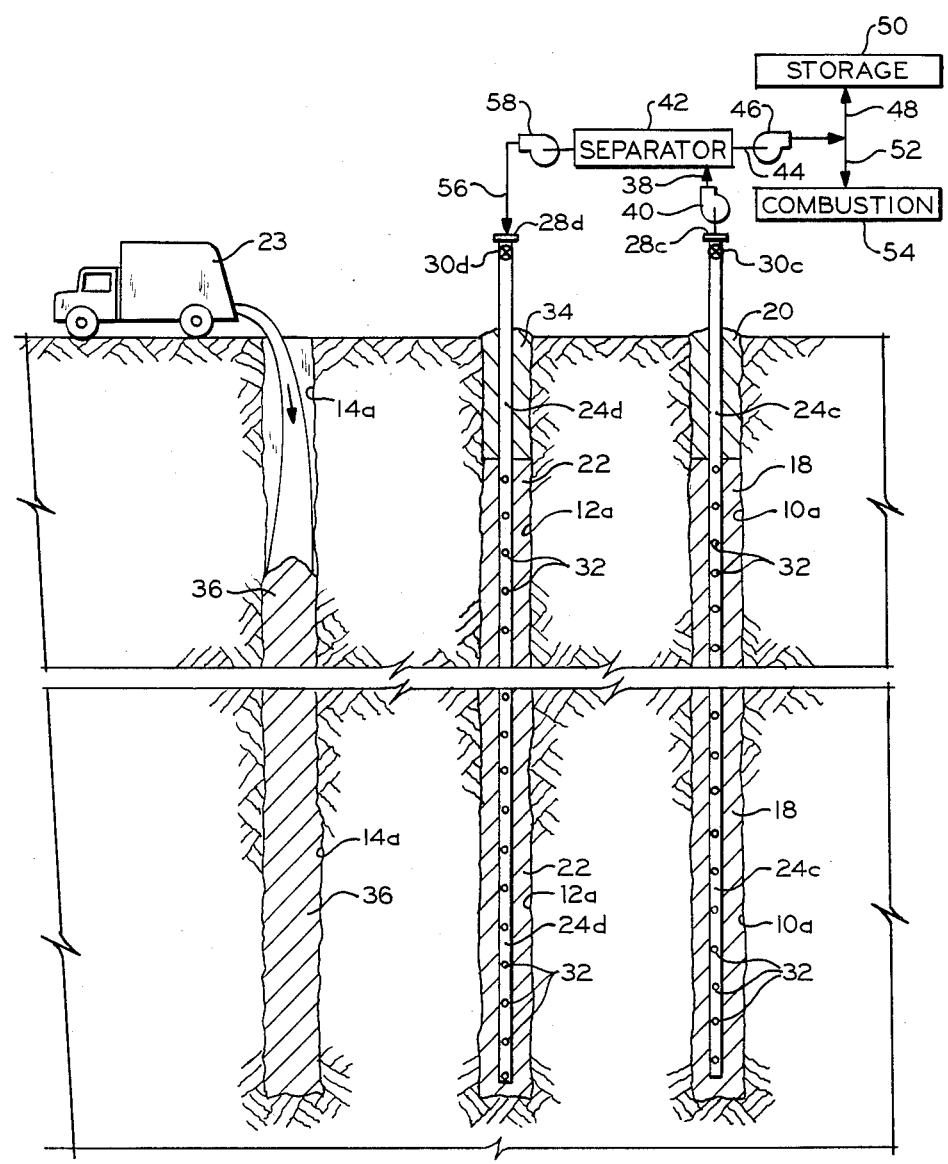
FIG. 7 is a diagrammatical representation in vertical cross section of an alternate form of the apparatus of the present invention showing first, second and third cavities in the earth in the form of vertical shafts bored in the earth.

FIG. 7 illustrates a variation of the process and apparatus of the present invention similar to that described above and depicted for FIG. 2. It will be seen, however, that the cavities 10a, 12a and 14a are in the form of vertical shafts which have been bored or drilled in the earth. The shaft or well 10a has been filled with waste material 18 and covered with earth 20. The waste material 18 and earth 20 has been penetrated by a suitable conduit 24c having a gas permeable portion preferably in the form of plurality of perforations or apertures 32 therein communicating between the interior thereof and the waste material 18. The upper end portion of the conduit 24c terminates in a suitable pipe connection 28c and preferably includes a shut-off valve 30c interposed therein adjacent the pipe connection 28c. Similarly, the shaft or well 12a has been filled with waste material 22 which has been covered with earth 34. The waste material 22 and earth 34 have been penetrated by a conduit 24d which is also provided with a gas permeable portion preferably in the form of perforation or aperture 32 therein communicating between the interior thereof and the waste material 22. The upper end portion of the conduit 24d preferably terminates in a suitable pipe connection 28d and further preferably includes a suitable shut-off valve 30d interposed therein adjacent the pipe connection 28d. The previously described conduits 38 and 56 are respectively connected in fluid flow communication with the pipe connections 28c and 28d, thus connecting the conduits 24c and 24d to the previously described separator 42 which functions in a manner described above.

It will be understood that the conduits 24, 24a, 24b, 24c and 24d can be provided with a suitable valve which will permit the maintenance of the apertures 32 in a closed position until such time as it is desired to produce product gas therethrough or inject carbon dioxide therethrough. Suitable surface actuated sleeve valves for such operations are well known in the art and may be readily adapted for use in the present invention.

In accordance with the present invention, it is estimated that a methane yield of 4 to 4.5 standard cubic feet of methane per pound of volume solids can be obtained. It is presently preferred that the temperature in each cavity during the anaerobic fermentation of the waste material therein will be in the range from about 40° C. to about 60° C., however, the fermentation temperature can drop to around 20° C. or lower but will slow the fermentation process. The temperature of the fermentation process can be controlled to some degree by the injection of water and/or nutrients into the waste material during the anaerobic fermentation process. The pH of the waste material during the anaerobic fermentation can be any pH which will permit the process to continue, but will generally be in the range from about 6.6 to about 7.6, and will preferably be in the range from about 7 to about 7.2. At a pH below about 6.2, little methane will be produced from the anaerobic fermentation of the waste material. In the anaerobic fermentation of manure, it is anticipated that the production of 20 to 24 cubic meters per day of biogas would require waste from approximately 20 cattle or 150 pigs, or 2500 chickens per day.

From the foregoing it will be seen that the method and apparatus of the present invention readily meet the stated objects of the present invention. Changes can be made in the combination and arrangement of parts or elements as heretofore set forth in the specification and shown in the drawings without departing from the spirit and scope of the invention as defined in the following claims.

I claim:
1. Apparatus for producing methane by anaerobic fermentation of waste material, comprising:
cavity means in the earth for holding a quantity of said waste material;
means for covering a quantity of said waste material in said cavity means and thereby separating said quantity of said waste material from the atmosphere;
first conduit means communicating between said waste material in said cavity means and a location remote from said cavity means for conveying gas comprising carbon dioxide and methane from said cavity means to said location;
gas separation means communicating with said first conduit means at said location for separating carbon dioxide from methane, said first conduit means including at least one pipe having a plurality of apertures therein and disposed in said cavity means extending into and in fluid flow communication with said waste material for receiving gas liberated by the anaerobic fermentation of said waste material and comprising carbon dioxide and methane, through said apertures therein for conveyance via said first conduit means to said gas separation means;

second conduit means communicating between said gas separation means and said waste material in said cavity means for conveying carbon dioxide from said gas separation means to said waste material; and third conduit means communicating with said gas separation means for conveying methane from said gas separation means.

2. Apparatus in accordance with claim 1 wherein said cavity means comprises two cavities in the earth each for holding a quantity of said waste material therein; wherein said means for covering a quantity of said waste material in said cavity means covers the quantity of said waste material held in each of said cavities; and wherein said first conduit means communicates with said waste material in a first one of said two cavities in the earth and said second conduit means communicates with said waste material in a second one of said two cavities in the earth.

3. Apparatus in accordance with claim 2 wherein each of said cavities is in the form of a shaft bored in the earth.

4. Apparatus for producing methane by anaerobic fermentation of waste material, comprising:

cavity means in the earth for holding a quantity of said waste material;

means for covering a quantity of said waste material in said cavity means and thereby separating said quantity of said waste material from the atmosphere;

first conduit means communicating between said waste material in said cavity means and a location remote from said cavity means for conveying gas comprising carbon dioxide and methane from said cavity means to said location;

gas separation means communicating with said first conduit means at said location for separating carbon dioxide from methane, said first conduit means including at least one pipe having gas permeable walls and disposed in said cavity means extending into and in fluid flow communication with said waste material for receiving gas liberated by the anaerobic fermentation of said waste material and comprising carbon dioxide and methane, through the gas permeable walls of said at least one pipe for conveyance via said first conduit means to said gas separation means;

second conduit means communicating between said gas separation means and said waste material in said cavity means for conveying carbon dioxide from said gas separation means to said waste material; and third conduit means communicating with said gas separation means for conveying methane from said gas separation means.

5. Apparatus in accordance with claim 4 wherein said cavity means comprises two cavities in the earth each for holding a quantity of said waste material therein; wherein said means for covering a quantity of said waste material in said cavity means covers the quantity of said waste material held in each of said cavities; and wherein said first conduit means communicates with said waste material in a first one of said two cavities in the earth and said second conduit means communicates with said waste material in a second one of said two cavities in the earth.

6. Apparatus for producing methane by anarobic fermentation waste material, comprising:

cavity mean in the form of an excavation dug in the surface of the earth for holding a quantity of said waste material;

means comprising earth disposed on top of said waste material for covering a quantity of said waste material in said cavity means and thereby separating said quantity of said waste material from the atmosphere;

first conduit means communicating between said waste material in said cavity means and a location remote from said cavity means for conveying gas comprising carbon dioxide and methane from said cavity means to said location;

gas separation means communicating with said first conduit means at said location for separating carbon dioxide from methane;

second conduit means communicating between said gas separation means and said waste material in said cavity means for conveying carbon dioxide from said gas separation means to said waste material; and third conduit means communicating with said gas separation means for conveying methane from said gas separation means.

7. Apparatus in accordance with claim 6 wherein said cavity means comprises two cavities in the earth each for holding a quantity of said waste material therein; wherein said means for covering a quantity of said waste material in said cavity means covers the quantity of said waste material held in each of said cavities; and wherein said first conduit means communicates with said waste material in a first one of said two cavities in the earth and said second conduit means communicates with said waste material in a second one of said two cavities in the earth.

8. Apparatus in accordance with claim 7 wherein the earth disposed on top of said waste maerial in a first one of said cavities comprises earth from an excavation dug in the surface of the earth to form a second one of said cavities.

9. Apparatus in accordance with claim 8 wherein said first conduit means includes:

at least one pipe having a plurality of apertures therein and disposed in said cavity means extending into and in fluid flow communication with said waste material for receiving gas liberated by the anaerobic fermentation of said waste material and comprising carbon dioxide and methane, through said apertures therein for conveyance via said first conduit means to said gas separation means.

10. Apparatus in accordance with claim 8 wherein said first conduit means includes:

at least one pipe having gas permeable walls and disposed in said cavity means extending into and in fluid flow communication with said waste material for receiving a gas liberated by the anaerobic fermentation of said waste material and comprising carbon dioxide and methane, through the gas permeable walls of said at least one pipe for conveyance via said first conduit means to said gas separation means.

* * * * *